United States Patent [19]

Schmidt et al.

[11] Patent Number: 5,122,246
[45] Date of Patent: Jun. 16, 1992

[54] FREE FLOW ELECTROPHORESIS METHOD

[76] Inventors: Joseph L. Schmidt, 40 Brighton 1st Rd., Apt. 15D, Brooklyn, N.Y. 11235; Huk Y. Cheh, 29-06 214 St., Bayside, N.Y. 11360

[21] Appl. No.: 721,303

[22] Filed: Jun. 26, 1991

[51] Int. Cl.$^5$ .................. B01D 57/02; B01D 61/42
[52] U.S. Cl. .......................... 204/180.1; 204/299 R
[58] Field of Search ............ 204/299 R, 180.1, 182.3, 204/182.4, 183.1

[56] References Cited

U.S. PATENT DOCUMENTS

| | | |
|---|---|---|
| 4,358,358 | Rhodes | 204/180.1 |
| 4,749,458 | Muroi et al. | 204/299 R |
| 4,758,320 | Sanchez et al. | 204/182.3 |
| 4,874,507 | Whitlock | 204/180.1 |

Primary Examiner—John Niebling
Assistant Examiner—Caroline Koestner

[57] ABSTRACT

The present invention relates to a free flow electrophoresis method between two ion permeable membranes comprising applying an electric field perpendicular to the primary carrier flow, applying a secondary carrier flow perpendicular to both the primary buffer flow and the electric field, simultaneously reversing the direction of the field and secondary carrier flow, and repeating the previous step until effective separation occurs.

17 Claims, 2 Drawing Sheets $o \leq t \leq T$ $T < t < 2T$

FREE FLOW ELECTROPHORESIS METHOD

The present invention relates to a free flow electrophoresis method between two ion permeable membranes comprising applying an electric field perpendicular to the primary carrier flow, applying a secondary carrier flow perpendicular to both the primary buffer flow and the electric field, simultaneously reversing the direction of the field and secondary carrier flow, and repeating the previous step until effective separation occurs.

Electrophoretic fractionations are generally performed in a gel or in a stream of free flowing electrolyte carrier. A typical gel electrophoresis technique comprises the electromigration of a small sample of a protein mixture through a slab of a porous gel matrix under an applied electric field. The individual components of the mixture generally each have a different electrophoretic mobility such that they all move at different velocities under the applied field whereby separation occurs over time. The gel is used to reduce thermal convection which arises from heat generated by the electric current which flows between the electrodes. The gel also serves as a molecular sieve in that a "drag" effect arises as the larger species try to move through the viscous media. Although gel electrophoresis is a common technique for analyzing different macromolecules, it can not be used to separate organelles and whole cells due to restrictions on the motion of such large species through gel. An additional drawback of gel electrophoresis is that recovery of the fractionated species from the gel is a difficult and time consuming operation.

Free flow electrophoresis is more amenable for fractionating charged species such as cells and macromolecules, i.e. procaryotic and eucaryotic cells, red blood cells and lymphocytes, cell organelles, viruses, chromosomes, inclusion bodies and membrane proteins. Continuous free flow electrophoresis (CFFE) is characterized by inducing each species in a heterogeneous sample to move in a second dimension, normal to the electrophoretic motion. The trajectory of each individual species is determined by the sum of the individual electrophoretic velocities and the carrier electrolyte velocity. The direction of the sum of these velocity vectors translates into a distinct exit position for each individual species. However, resolution is hampered by the spreading of the bands of individual species during migration.

A typical CFFE system has two parallel plates forming a vertical separation chamber therebetween. An electrode is located on each side of the chamber. A continuous downward flow of a carrier buffer solution passes through the chamber. A narrow streak of a heterogeneous sample of the species to be separated is introduced at the upper end of the chamber. A uni-directional electric field is applied between the electrodes whereby the species to be separated move in the direction of the field in accordance with their electrophoretic mobilities as well as moving downwardly with the buffer flow. The net effect of the combination of these two movements is that the species are separated into multiple bands and can be collected at the lower end of the chamber using multiple collection ports.

Extensive research efforts have been devoted to continuous free flow electrophoresis but its use is hampered by poor resolution and complexity of the apparatus. Poor resolution is caused by several factors including a phenomena called crescent flow. Crescent flow arises from a parabolic velocity profile of the fluid carrier whereby the fluid in the center of the stream flows faster than the fluid near the walls of the fractionation chamber. This results in uneven residence time for dispersed species. Electroosmotic flow and thermally induced convection also contribute to the poor resolution.

Lightfoot et al. (NIH Publication 78-1422, 463 (1978)) describes an electrophoretic method which uses a periodic unidirectional electric field to fractionate a mixture of charged species inside a hollow fiber membrane. A small volume of the sample is introduced into the fiber and an electric field is applied across the fiber for a limited period of time, pushing the species toward the fiber wall at a rate dependent on their electrophoretic mobilities. After the field is terminated the separated species exit the hollow fiber at different intervals. This method is limited by poor resolution and the difficulty of scaling up using a bundle of hollow fibers.

Schwartz and Cantor (Cell, Vol. 37, 67 (1984)) disclose using a two dimensional alternating field for fractionating DNA fractions in a gel. The use of an alternating electric field is also disclosed by Giddings (Anal. Chem., Vol. 58, 2052 (1986)) wherein the method comprises cycling the field strength together with changing the direction of sedimentation, thermal diffusion, cross-flow of buffer, electric field, or magnetic field.

Cyclical-field flow fractionation using gravity has also been employed wherein the method comprises changing the orientation of the separation chamber relative to the gravitational field. A one dimensional separation occurs along a single principle flow axis. This method is limited in throughput because separation is periodical where the fractionated species flow out from the separation chamber through the same flow outlet but at different intervals.

An object of the present invention is to provide an electrophoretic method having a higher selectivity and throughput than the above described methods.

The features and advantages of the present invention are described below in reference to the drawings in which.

The present invention is a method for the electrophoretic separation of charged species between two membranes, which method comprises the use of an alternating electric field, a continuous, primary flow of buffer solution, and a secondary buffer flow which is created by moving one of the membranes in a reciprocating fashion. The three dimensional movement improves resolution and increases throughput.

Figure 1:
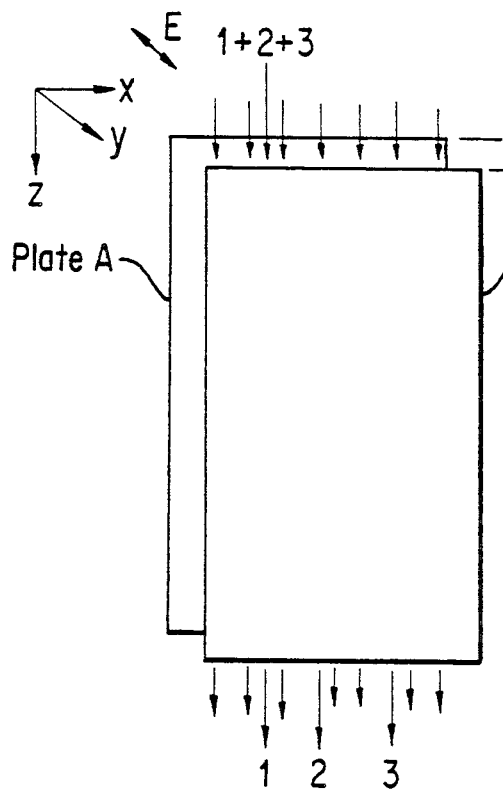
FIG. 1 is a schematic representation of a fractionation chamber for use with the present invention.
Figure 2A:
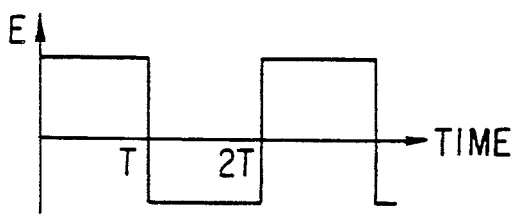
FIG. 2a is a plot of the applied electric field versus time.
Figure 2B:
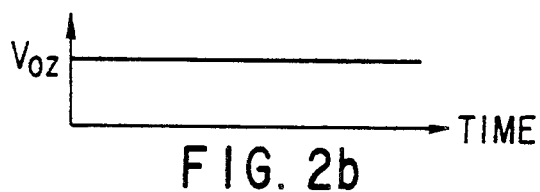
FIG. 2b is a plot of the primary buffer flow versus time.
Figure 2C:
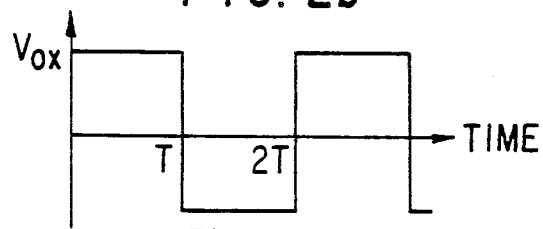
FIG. 2c is a plot of the moving membrane velocity versus time.
Figure 2D:
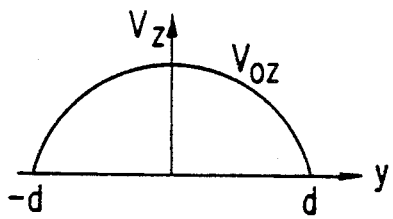
FIG. 2d is a profile of the primary buffer flow velocity plotted as a function of the distance between the membranes.

In particular, the method comprises introducing a mixture of charged species into a continuous, downward flow of buffer solution (hereinafter called the "primary" flow) between two ion permeable membranes. FIG. 1 is a schematic view showing stationary membrane plate A and reciprocating membrane plate B. The primary buffer flow direction is shown in the downward direction along the z axis. This flow has a constant velocity as shown in FIG. 2b. A mixture of charged species, designated "1+2+3", is shown being introduced into the primary buffer flow at the upper portion of the gap between the stationary and reciprocating membrane. The mixture of charged species can either be introduced as a single sample or as a continuous stream from a reservoir. An electric field is applied between a pair of electrodes which are positioned one behind plate A and one behind plate B. Thus, the direction of the applied alternating field is along the $\pm y$ dimension. FIG. 2a shows a graph of the voltage applied versus time. Depending on the electric charge of the species (i.e. positive or negative) they are each attracted to one electrode and repulsed by the other. Plate B moves in the $\pm x$ direction in a motion synchronized with the frequency of the electric field. FIG. 2c shows a graph of the velocity of plate B versus time. Each time the polarity of the field is changed the direction of the plate movement along the x axis is reversed (compare FIGS. 2a and 2c).

Figure 2E:
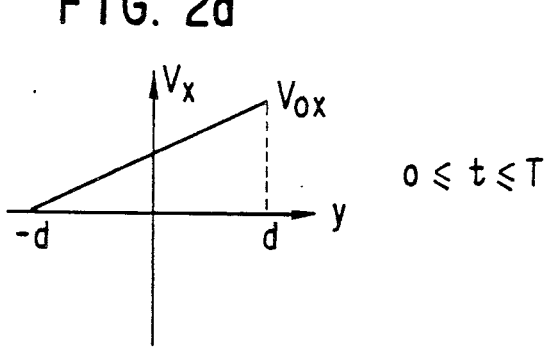
FIG. 2e is a plot of the buffer flow velocity attributed to the membrane movement during the first half cycle versus the distance between the membranes.
Figure 2F:
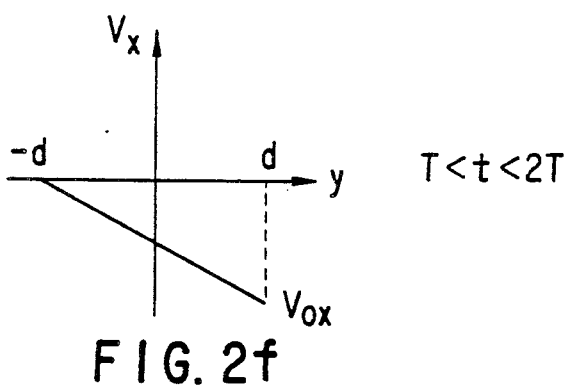
FIG. 2f is a plot of the buffer flow velocity attributed to the membrane movement during the second half cycle versus the distance between the membranes.

The membrane movement causes an additional buffer flow in the direction of the plate movement, which buffer flow has a velocity at the plate surface substantially equal to the plate velocity but which decreases linearly in the direction toward plate A where there is substantially zero buffer flow in the direction of the movement of plate B. FIG. 2e is a graph of the buffer velocity across the gap between the membranes due to the movement of membrane plate B during the first half cycle (i.e. $0 < t < T$). At the surface of membrane A the buffer velocity is substantially zero while at the surface of membrane B the buffer velocity is substantially equal to the membrane velocity, $V_{ox}$, and the buffer velocity varies linearly therebetween. FIG. 2f shows the buffer velocity profile during the second half cycle after the direction of membrane B movement is reversed. Thus, a charged particle near plate B will move as plate B moves whereas a particle near plate A will not move at all in the direction of plate B's movement.

Each charged species in the mixture follows a unique trajectory which is determined by its electrophoretic mobility, the primary flow of buffer, and the flow of buffer caused by the plate movement. Slower migrating species spend a greater amount of time in the primary flow than do faster species since once a species reaches one of the plates it stops moving with the primary flow. Therefore, slower species move a greater distance with the primary flow during each cycle than do faster species. On the other hand, the faster species move a greater distance with the moving plate since they reach the plate before the slower species.

The net effect of the application of three different forces on the separation of charged species is as follows. The mixture of charged species is introduced into a constant downward flow of primary buffer between two membranes. An electric field is applied perpendicular to the primary flow causing the charged species to move with the field, each at a velocity in the direction of the field that is dependent on its electrophoretic mobility. Faster migrating species move from one membrane wall to the opposite in less time during each cycle than slower species, and, as a result, move less downward than the slower species due to the lower buffer flow at the membrane surface. Once the faster species reach the membrane surface they remain there until the field polarity is reversed. Adsorption of species at the membrane surface is minimized due to the short residence time and the non-adsorbing nature of the membrane.

Simultaneously with applying the electric field, one of the membranes is moved side to side in a direction perpendicular to both the primary buffer flow direction and the field direction. As discussed above, the membrane wall movement results in a substantially linear velocity gradient, wherein the buffer velocity at the moving membrane is substantially equal to the membrane velocity whereas velocity at the stationary membrane is substantially zero. The membrane velocity should be relatively low so as not to promote vortex formations, especially during reversal of the membrane velocity. During each time cycle the velocity of the faster migrating species in the direction of the wall movement increases as they approach the moving membrane. Once they reach the membrane they move with it until the membrane stops. On the other hand, the slower migrating species take longer to reach the moving membrane surface and, as a result, they move a lesser distance in the direction of the membrane movement than the faster species. When the direction of both the field and membrane movements are reversed all the charged species move in the field direction toward the stationary wall. The faster migrating species reach the stationary wall first and, as a result, they move a lesser distance with the moving membrane during this half of the cycle whereas the slower species, being closer to the moving membrane, move a greater distance. The net effect of the reciprocating wall movement is that the separation between the faster and slower species increases with each half period. Further, since the faster migrating species travel less downwardly during each time cycle it takes more cycles for the faster species to travel the length of the fractionation gap. The increased number of cycles further increases the separation between the faster and slower species in the dimension parallel to the membrane movement (i.e. the x dimension in the figures). It is preferred that at least 10 cycles are completed, more preferably at least 20 cycles are completed, and most preferably at least 40 cycles.

It is preferred that the sample is introduced near the stationary membrane so that full advantage is taken in the first cycle of the buffer flow velocity gradient due to the membrane movement. However, it is possible that the sample inlet stream could be at any location between the membranes or could even be a stream having a width about the same as the distance between the membranes. In either of these latter less preferred arrangements there would be an added dispersion effect which can be alleviated by having the species go through at least 20, and more preferably at least 40 cycles before they exit the chamber.

The magnitude and frequency of the primary electric field, the rate of primary buffer flow, and the frequency of membrane movement are all dependent on the size of the fractionation chamber being used and the electrophoretic mobilities of the species to be separated. Generally, the species being separated are known species so that their mobilities are known. Once a particular size of a fractionation chamber is chosen it is well within the skill of the artisan to optimize the electric field, the rate of primary buffer flow, and the membrane movement in order to separate the particular mixture of interest. The following discussion and calculations demonstrate the separation method of the present invention for a hypothetical mixture. However, the same considerations apply for separating a known mixture.

In the following calculations the coordinate system shown in FIG. 1 relative to the membrane plates is used. The mixture of three charged species "1+2+3" is injected near the surface of membrane A which has a y coordinate of $-d$. The surface of reciprocating plate B has a y coordinate of $+d$ so that the gap between plates A and B is $2d$. The electrophoretic mobility of a species to be separated is $\mu_n$, while $\mu_T$ is the electrophoretic mobility of a hypothetical species which will migrate the distance $2d$ in exactly one half of a full time cycle. A full time cycle is the sum of the time that the electric field is applied in one direction plus the time that the field is applied in the opposite direction (see FIG. 2a where the full cycle equals 2T). This is also the full time cycle of the movement of Plate B (see FIG. 2c). The value of $\mu_T$ is significant because only species having an electrophoretic mobility greater than this value will be separated by the present method. Species having an electrophoretic mobility less than this would elute from the fractionation chamber at the same "x position" they were introduced at. This is discussed more fully below.

At any time, t, during the first half of the time cycle ($0<t<T$) the position of a species "n" in the y dimension is $$y = -d + \mu_n E t \qquad (1)$$

where E is the strength of the electric field. The distance traveled by species "n" with the primary buffer flow in the z direction is $$\Delta z_A = \int_{-d}^{d} \frac{V_{oz}}{\mu_n E}\left(1 - \frac{y^2}{d^2}\right) dy = \frac{4 V_{oz} d}{3 \mu_n E} \qquad (2)$$

where Voz is the velocity of the primary buffer flow.

The distance traveled by species "n" in the x dimension (caused by the membrane movement) has two components. The first component is due to the movement of the buffer between the plates caused by the plate movement and is given by $$\Delta x_1 = \frac{V_{ox}}{2\mu_n E} \int_{-d}^{d} \left(\frac{y}{d} + 1\right) dy = \frac{V_{ox} d}{\mu_n E} \qquad (3)$$

where is Vox the velocity of the moving plate. The second component is the component which causes the separation of the charged species. This component is due to the fact that all of the species being separated will reach plate B in a time less than T so that they will travel at plate B's velocity, Vox, for some fraction of the half cycle. The length of time a given species travels with plate B depends on its unique electrophoretic mobility since the latter determines when a species will reach plate B under the applied electric field. This component is given by $$x_2 = \left(\frac{2d}{\mu_T E} - \frac{2d}{\mu_n E}\right) V_{ox} \qquad (4)$$

so that the total movement of species "n" in the x dimension during the first half cycle is given by $$\Delta x_A = x_1 + x_2 = \frac{V_{ox} d}{\mu_n E} + \left(\frac{2d}{\mu_T E} - \frac{2d}{\mu_n E}\right) V_{ox} \qquad (5)$$

The movement of species "n" during the second half of the time cycle (T<t<2T) is as follows. Movement in the y dimension caused by the electric field is given by $$y = d - \mu_n E t \qquad (6)$$

Movement with the primary buffer flow in the z dimension is the same as during the first half cycle, namely $$\Delta z_B = \frac{4 V_{oz} d}{3 \mu_n E} \qquad (7)$$

Movement in the x dimension has only one component since once the species reach plate A there is no movement in the x dimension. Thus, movement in the x dimension is only due to the buffer flow caused by plate B's velocity during the second half cycle ($-V_{ox}$) and is given by $$\Delta x_B = \frac{-V_{ox} d}{\mu_n E} \qquad (8)$$

so that the movement in the x dimension during a full cycle, 2T, is given by $$\Delta x_T = \Delta x_A + \Delta x_B = \left(\frac{2d}{\mu_T E} - \frac{2d}{\mu_n E}\right) V_{ox} = \frac{V_{ox} d}{E}\left(\frac{2\mu_n - 2\mu_T}{\mu_n \mu_T}\right) \qquad (9)$$

The components during each half cycle attributable to the buffer flow caused by the plate movement cancel each other out so that the net movement in the x direction is caused solely by the time that a species moves while it is at the surface of plate B. This expression shows that movement in the x dimension is dependent on the electrophoretic mobility, $\mu_n$, of each species since all of the other variables in this expression are fixed for a given fractionation run. This expression also shows that when the electrophoretic mobility of any species, $\mu_n$, is less than $\mu_T$ there is no movement in the positive x direction.

The total movement in the x dimension of a species "n" during an entire fractionation process is the expression given above multiplied by the total number of cycles it takes for the species to travel the length of the fractionation chamber, L. The total number of cycles, N, for species "n" to travel the distance L is found by dividing L by the distance traveled in the z direction during a full cycle and is given by $$N = \frac{L3\mu_n E}{8 V_{oz} d} \quad (10)$$

Therefore, movement in the x direction of species "n" as it travels from the top to the bottom of the fractionation chamber during the present method is equation (9) multiplied by equation (10) or $$x_T = \frac{3L V_{ox}}{4 V_{oz}} \left( \frac{\mu_n}{\mu_T} - 1 \right) \quad (11)$$

This last expression is used to determine the ultimate separation of the species in the mixture.

The ability of the present invention to provide effective separation of species having relatively close electrophoretic mobilities is demonstrated using this expression. A typical fractionation chamber is 40 cm long (L) and has the two membranes separated by about 0.1 cm (2d). The primary buffer flow velocity ($V_{oz}$) is about 0.15 cm/s and the velocity ($V_{ox}$) of moving membrane B is about 0.1 cm/s. A typical electric field strength (E) is about 100 volts/cm and a full time cycle (2T) is about 20 seconds. The value of the electrophoretic mobility of the hypothetical species which travels the distance 2d in time T is given by $$\mu_T = \frac{2d}{ET}$$

and calculates out to be 1 micron/s per volt/cm. A mixture of three species "1+2+3" having respective electrophoretic mobilities of $\mu_1 = 1.0$, $\mu_2 = 1.1$, and $\mu_3 = 1.2$ microns/s per volt/cm would be separated as follows. Species "1" does not move at all in the x direction since it has an electrophoretic mobility such that it travels between the membranes in one half cycle. Species "2", however, would travel 2 cm in the x direction, and species "3" would travel 4 cm. Thus, by providing appropriately exit ports at the end of the fractionation chamber the three separated species can be collected.

By way of comparison, the same three species described immediately above separated using conventional free flow electrophoresis in a chamber 40 cm long, with a buffer flow of 0.1 cm/s, and a field strength of 100 volts/cm would deviate from their original position by 4.0, 4.4, and 4.8 cm respectively. The present invention clearly provides much better separation over the same length fractionation column. Additionally, the present invention provides better separation at a 50% higher throughput in the example so that the more of the separated species can be collected in a given time period.

Once the mixture of species to be separated is known the values of E, 2d, T, L, $V_{ox}$, and $V_{oz}$ can be optimized to provide the desired separation.

Figure 3:
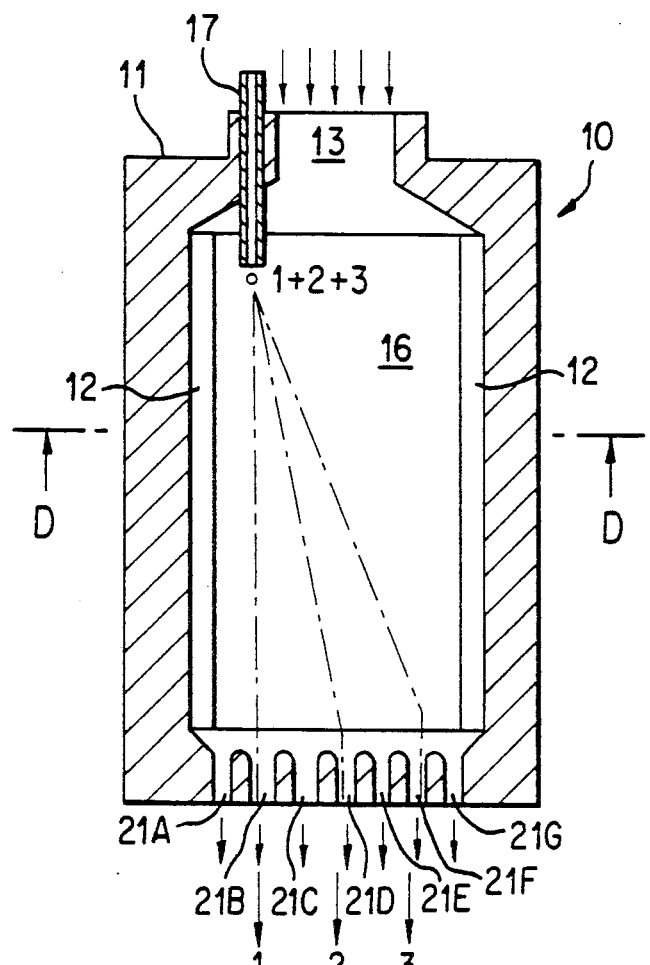
FIG. 3 is a cut away view through a fractionation chamber in accordance with the present invention.
Figure 4:
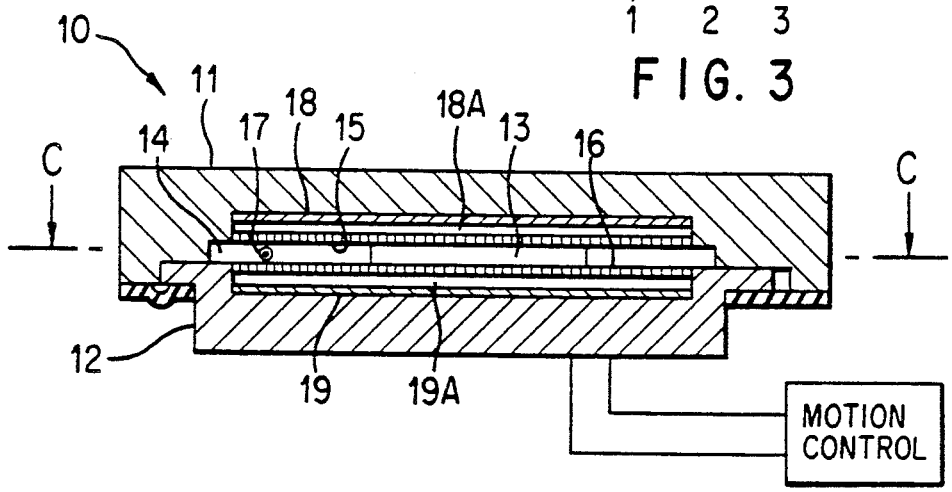
FIG. 4 is cross sectional view through the fractionation chamber shown in FIG. 3.

An embodiment of a fractionation chamber for carrying out the present invention will be discussed with reference to FIGS. 3 and 4. FIG. 3 shows a schematic vertical cross-sectional view through a rectangular fractionation chamber 10 taken through the center of the fractionation gap (line C—C in FIG. 4) and FIG. 4 shows a schematic horizontal cross-sectional through line D—D in FIG. 3. Chamber 10 comprises stationary housing plate 11 and reciprocating housing plate 12. Plate 12 is moved side-to-side by using any well known motion control means (not shown). Housing plates 11 and 12 are preferably made from a solid non-electrically conducting material such as any of the well known machining plastics including but not limited to polyolefins, polycarbonates, polyhalohydrocarbons, and polyvinylchlorides. Alternatively, housing plates 11 and 12 can be made from metal with the internal surfaces of the plates coated with an electrically non-conducting material.

Rectangular, ion permeable membrane 15 is fixed to the internal surface of housing plate 11 and is superimposed over rectangular electrode 18. Preferably a gap 18a is provided between membrane 15 and electrode 18 so that electrolyte can be circulated through the gap to remove Joule heat. Rectangular, ion permeable membrane 16 is fixed to the internal surface of housing plate 12 and is superimposed over rectangular electrode 19. Preferably a gap 19a is provided between membrane 16 and electrode 19 for the reasons described above.

Membranes 15 and 16 are preferably comprised of an ion-permeable glass plate or any other electrically non-conducting material such as ceramics or polymers. The membranes should be dimensionally stable and non-absorbing. A variety of techniques are known for controlling adsorption and electroosmotic flows through the membrane. These techniques include chemical treatment of the glass and/or casting a suitable polymer membrane into the surface of the porous glass or ceramic matrix. The pores of the membrane should be sufficiently small so as to preclude leakage or penetration of the charged species across the membrane. Preferably, the pore sizes should be several times smaller than the smallest charged species being separated. For example, for separating proteins a preferred membrane would be a dialyzing membrane with pore sizes having a cutoff value of a few hundred dalton molecular weight.

Gap 14 between membranes 15 and 16 is the fractionation gap across which the charged species migrate under the influence of the electric field applied between electrodes 18 and 19. Opening 13 is provided at the upper end of chamber 10 to supply the primary buffer flow through gap 14. Exit ports 21a–21g are provided at the opposite end of the fractionation chamber for collecting the separated charged species. Sample inlet tube 17 is located at the upper end of the fractionation chamber. Alternatively, the sample inlet tube could be located at 90° to the position shown going back into the page so that the sample tube would project through membrane 16 and introduce the sample stream into the primary buffer flow at about the same position shown.

Housing plate 12 is reciprocatingly attached to housing plate 11 a described above. Rubber gasket 20 or any other appropriate sealing means is provided to seal the interface area between the plates so a to prevent leakage of the primary buffer flow.

Embodiments other than the one described above are possible for practicing the present invention. Common features among the embodiment described and other possible embodiments include those elements for creating the orthogonal, three dimensional separation forces, namely (1) a fractionation gap between membranes for the primary buffer flow, (2) electrodes placed on opposite sides of the gap for effecting an electric field, and (3) a reciprocating membrane having its movement at 90° to the buffer flow and the electric field. Conventional means for pumping the primary buffer flow, cooling the electrodes, introducing the sample, and collecting the separated species are available and are suitable for use with a fractionation chamber designed to practice the present invention.

While it is preferred that the directions of the buffer flow, the electric field, and the plate movement are all at about right angles to each other it is possible to vary these angles to something other than 90° to achieve different separation effects.

The examples and figures are for illustrative purposes only and should not be interpreted to impose any limitations on the invention as claimed.

What is claimed is:

1. A free flow electrophoretic method for separating a mixture of charged species comprising introducing a mixture of charged species into a buffer solution flowing through a gap between a fixed membrane and a reciprocating membrane; applying an electric field at about a right angle to and across membrane gap; moving the reciprocating membrane simultaneously with applying the field, said movement being in a direction at about right angles to both the buffer flow and electric field direction; simultaneously reversing the direction of the field and the direction of reciprocating membrane movement; and repeating the previous step until effective separation of the charged species occurs downstream from where the mixture was introduced.

2. The method of claim 1 wherein the time period for both applying the field and moving the membrane is about the same for both the forward and reverse directions.

3. The method of claim 1 wherein the time period for applying the field and moving the membrane is such that when the field direction is inducing the species to move toward the reciprocating membrane at least one species reaches said membrane and moves with said membrane.

4. The method of claim 1 comprising continuously introducing the mixture through an inlet port near the surface of the fixed membrane.

5. The method of claim 1 wherein the direction of the field and the direction of the membrane movement are reversed at least 20 times.

6. A method for separating a mixture of electrically charged species in a free flowing buffer stream, wherein at least one species has an electrophoretic mobility greater than a predetermined electrophoretic mobility of $\mu_T$ microns/s per volt/cm, comprising passing a buffer solution through a gap between a fixed plate and a reciprocating plate; introducing a mixture of the charged species into the buffer flow; applying an electric field in one direction across the buffer flow for a first time period sufficient for a charged specie having an electrophoretic mobility of $\mu_T$ microns/s per volt/cm to move with the field a distance substantially equal to the gap between the plates and simultaneously moving the reciprocating plate in a direction different from the buffer flow direction and the field direction for a time period about equal to the first time period; simultaneously reversing the direction of the field and the direction of the plate for a second time period about equal to the first time period; and repeating the previous step at least 10 times to effectively separate the charged species having an electrophoretic mobility greater than $\mu_T$ microns/s per volt/cm.

7. The method of claim 6 wherein the buffer flow is in a downward direction.

8. The method of claim 7 wherein the electric field is applied at about right angles to the buffer flow.

9. The method of claim 8 wherein the reciprocating plate moves side-to-side at about right angles to the buffer flow and the field direction.

10. A method for separating a mixture of charged particles comprising supplying a primary flow of a conductive solution in a first direction through a gap between two plates; introducing a mixture of charged particles having at least two different electrophoretic mobilities into the primary flow; applying an electric field in a second direction that traverses the first direction until at least one particle-type of the mixture crosses the distance between the plates and simultaneously applying a secondary flow of conductive solution in a third direction that traverses both the first and second directions for about the same time period that the field is applied; simultaneously reversing the direction of the field and the direction of the secondary flow for about the same time period as in the previous step; and repeating the cycle step as many times as is necessary to effectively separate the charged particles in the primary solution flow downstream from where the mixture is introduced.

11. The method of claim 10 wherein the secondary flow velocity is a gradient such that the velocity near one plate is higher than the velocity near the other plate and said velocity varies linearly between said plates.

12. The method of claim 10 comprising moving one of the plates in a reciprocating manner to cause the secondary flow in the forward and reverse directions while the other plate remains fixed.

13. The method of claim 12 wherein the first direction is downwardly, the second direction is at about right angles to the first direction, and the third direction is at about right angles to said first and second directions.

14. The method of claim 13 comprising continuously introducing said mixture of charge particles into the primary flow.

15. The method of claim 13 comprising introducing said mixture through an inlet port in close proximity to the fixed plate.

16. The method of claim 10 comprising reversing the direction of the field and the direction of the secondary flow at least 20 times.

17. The method of claim 10 comprising reversing the direction of the field and the direction of the secondary flow at least 40 times.

* * * * *